Figure 1:
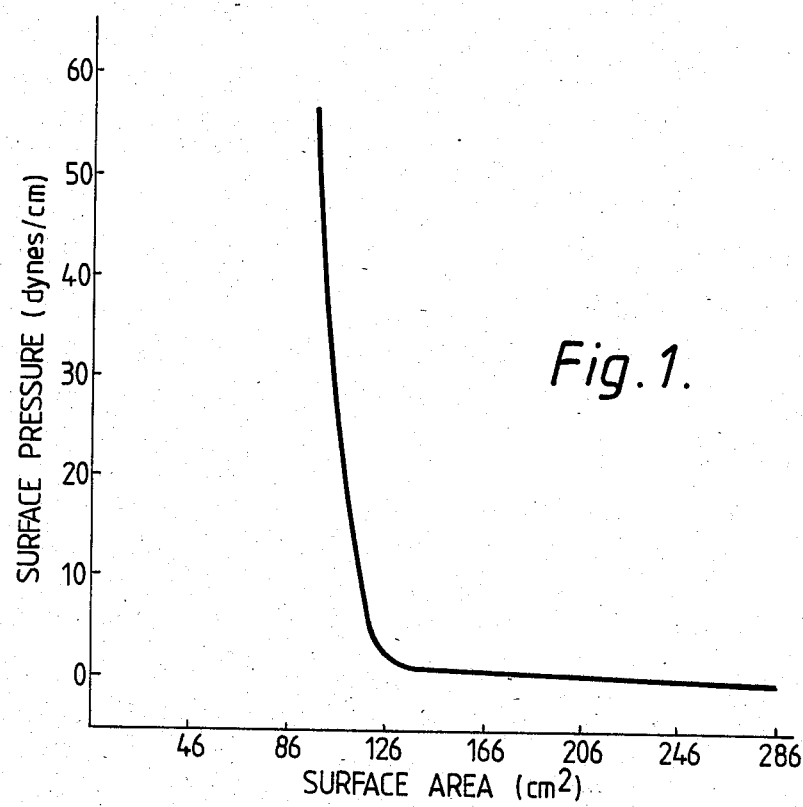

United States Patent [19]

Roberts et al.

[11] Patent Number: 4,584,235
[45] Date of Patent: Apr. 22, 1986

[54] THIN FILMS OF PHTHALOCYANINE ON SUBSTRATE

[75] Inventors: Gareth G. Roberts, Durham; Martyn V. Twigg, Yarm, both of England

[73] Assignee: Imperial Chemical Industries PLC, London, England

[21] Appl. No.: 662,134

[22] Filed: Oct. 18, 1984

Related U.S. Application Data

[63] Continuation of Ser. No. 420,575, Sep. 20, 1982, abandoned.

[30] Foreign Application Priority Data

Sep. 25, 1981 [GB] United Kingdom ............... 8129018

[51] Int. Cl.$^4$ ............................................. B05D 1/18
[52] U.S. Cl. .................................... 428/333; 427/58; 427/434.3; 428/336; 428/411.1
[58] Field of Search ...................... 428/411, 333, 336; 427/58, 434.3

[56] References Cited

PUBLICATIONS

Paper on Technological Applications of Langmuir-Blodgett Films, Roberts, Vincett and Barlow, Phys. Technol., vol. 12, 1981, p. 69.

*Primary Examiner*—Marion C. McCamish
*Attorney, Agent, or Firm*—Cushman, Darby & Cushman

[57] ABSTRACT

A method of preparing a thin film of a phthalocyanine compound on a substrate comprising forming a thin layer of the phthalocyanine compound on the surface of a suitable liquid and passing the substrate through the layer so that a film of the phthalocyanine is deposited upon the surface of the substrate. Very thin films are formed and the resulting composite articles are useful in the manufacture of electronic, electrical, electrochemical and photochemical devices of high sensitivity.

11 Claims, 10 Drawing Figures

THIN FILMS OF PHTHALOCYANINE ON SUBSTRATE

This is a continuation of application Ser. No. 420,575, filed Sept. 20, 1982, now abandoned.

This invention relates to a method of applying thin films to substrates, especially thin films of phthalocyanine compounds.

The application of thin films of organic compounds to solid substrates using the Langmuir trough technique is well known. Films made in this way are of interest for a number of applications especially in the electronics and biological fields.

Thus, in our UK Patent Specification No. 1572182 there is described a method of preparing an electrical, electrochemical or photochemical device comprising a sheet or film of organic material, said sheet or film having a high degree of molecular orientation, upon a substrate, the method comprising forming a very thin layer of an organic material having a planar delocalised system of $\pi$-electrons upon the surface of a suitable liquid and repeatedly passing a substrate through the layer so that a film of the organic material is deposited upon the substrate. Devices which include a thin film of organic material applied to a substrate by the same method are also described in our UK Patent Specification No. 1572181.

The organic materials proposed for film formation in the aforesaid patent specifications include a variey of homocyclic and heterocyclic compounds.

It has now been discovered that films having extremely useful properties can be produced by this method when the organic material used is a phthalocyanine.

The electrical properties of thin films of phthalocyanine compounds have been the subject of several studies in recent years. For example, Fan and Faulkner (J. Chem. Phys., 69, 3334, 3341, (1978)) have studied the photovoltaic and rectification properties of thin film cells in which a film (about 3000Å in thickness) of metal-free phthalocyanine or its zinc complex was sandwiched between films of gold and either aluminium or indium. The same authors have examined (J. Amer. Chem. Soc., 101, 4779, (1979)) the properties of metal-free, zinc and nickel phthalocyanine thin films (40–3000Å) as semiconductor electrodes. In these studies, the phthalocyanine thin films were deposited on the substrate by vacuum sublimation.

More recently, UK patent application No. GB 2077437A has described ammonia gas sensors, the operation of which is dependent upon the variation in electrical resistance of a layer of copper phthalocyanine (100–10,000Å) overlying suitably spaced electrodes. The method of depositing the phthalocyanine layer is not disclosed.

An important factor in the application of thin films to substrates is that the film should be of uniform thickness and especially that it should be free from holes. This becomes of increasing importance in the preparation of very thin films. Another important factor is that the preparation of films of a given thickness should be reproducible. In these respects, the methods of deposition hitherto described for phthalocyanines, such as vacuum sublimation and solvent evaporation, have not been entirely satisfactory. The method proposed herein minimises this problem in that it permits the preparation of phthalocyanine films of uniform and reproducible thickness. Furthermore, the method allows the preparation of thinner phthalocyanine films than can conveniently and reliably be prepared by other methods and facilitates the manufacture of more efficient electrophotographic, photovoltaic and other photo-electric devices including memory structures and those utilising the principle of photo-injection.

Thus according to the invention, there is provided a method of preparing a thin film of a phthalocyanine compound on a substrate which comprises forming a thin layer of the phthalocyanine compound on the surface of a suitable liquid and passing the substrate through the layer so that a film of the phthalocyanine is deposited upon the surface of the substrate.

The phthalocyanines are a well defined class of compounds and have been described in, for example, "The Chemistry of Synthetic Dyes", edited by K. Venkataraman, published by Academic Press Inc., in volume II, pp 1118–1142 and Volume V pp 241–282. Phthalocyanine compounds which may be used in accordance with the invention include the parent metal-free compound, the various metal complexes and the nuclear-substituted derivatives of such compounds with or without axial ligands co-ordinated to the metal atom.

The general method of forming a thin layer of an organic compound on the surface of a supporting liquid has been described in the prior art, and usually involves applying to the surface of the liquid an appropriate volume of a solution of the organic compound in a volatile solvent which is less dense than, and immiscible with, the supporting liquid and allowing the solvent to evaporate. Preferably, the supporting liquid is not a solvent for the organic compound and, for convenience, it is usually water in which case the volatile solvent will be a water-immiscible organic solvent of suitable density.

This method may be used to form thin layers of phthalocyanine compounds having suitable solubility characteristics.

The method of the invention generally involves, therefore, applying to the surface of the supporting liquid an appropriate volume of a solution of a phthalocyanine compound in a volatile organic solvent which is less dense than, and immiscible with, the supporting liquid and allowing the solvent to evaporate forming a thin layer on the surface of the supporting liquid of a phthalocyanine compound which is insoluble in said liquid. In some cases it may be advantageous to use a mixture of organic solvents. Thus, where the most suitable solvent for a particular phthalocyanine compound is a water-miscible solvent, this will normally be used in admixture with a water-immiscible solvent.

The successful operation of the method of the invention depends in large degree upon the selection of phthalocyanine compounds having suitable solubility characteristics. In this connection, it will be appreciated that the most frequently encountered phthalocyanines, for example copper phthalocyanine and the metal-free compound, are practically insoluble in organic solvents as are many other phthalocyanines. There are, however, several phthalocyanine compounds which are significantly soluble in selected organic solvents. These include some simple metal phthalocyanines, for example di(alkali metal) phthalocyanines such as the dilithium compound, phthalocyanines carrying organophilic substituents and phthalocyanines associated with other organic molecules in the form of complexes or adducts.

Thus, solutions in organic solvents may be formed of phthalocyanines having the general formula:

$Pc(Y)_n$ wherein Y is a solubilising group, n is an integer from 1 to 16, preferably 4 or 8, and Pc represents a phthalocyanine nucleus which may be metal-free or may contain a metal atom, for example Cu, Ni, Co, Fe, Mn, Cr, V, Pd, Pt, Zn or a lanthanide metal. Suitable solubilising groups include hydrocarbon groups such as alkyl, for example t-butyl, and aryl groups and groups of the formulae —NHR, —NR$_2$, —SO$_2$R, —SO$_2$NHR, —SO$_2$NR$_2$ and —SiR$_3$ wherein R represents a hydrocarbon radical such as alkyl or aryl.

Whilst it is usually desirable for the supporting liquid to be inert towards the phthalocyanine compound which is applied to its surface in solution form, this is not always so. Thus, in some cases it may be desirable to apply to the surface of the supporting liquid a solution of a first phthalocyanine compound which reacts with the supporting liquid to form a second phthalocyanine compound which may be relatively insoluble. To assist reaction between the first phthalocyanine compound and the supporting liquid, it can be advantageous for the first phthalocyanine compound to be in solution in a mixture of mutually miscible liquids one of which is miscible with, and one of which is immiscible with, the supporting liquid.

Thus, dilithium phthalocyanine is soluble in a number of organic solvents, for example ethanol and acetone. A solution of dilithium phthalocyanine in a mixture of a water-miscible solvent such as acetone and a water-immiscible liquid such as toluene or chloroform can be placed on an aqueous surface. Hydrolysis of the dilithium phthalocyanine takes place to form a layer of insoluble metal-free phthalocyanine. Alternatively, if the supporting liquid contains dissolved ions of metals which form insoluble phthalocyanines (for example, the first row transition metals, the precious metals or lanthanide metals), a layer of the corresponding metal phthalocyanine can be formed. When the supporting liquid is water, there will be competition between the metal ions and hydrogen ions for the phthalocyanine but under appropriate conditions of metal ion concentration and pH, the metal derivative is formed. Competition with hydrogen ions may be reduced by partially or wholly replacing water as supporting liquid by another suitable material such as methanol or ethanol. In some cases, it may be desirable, by suitable selection of reactants and reaction conditions, to form layers, and subsequently thin films on a substrate, containing two or more metal phthalocyanines with or without the metal-free compound.

Similarly, di(alkali metal) phthalocyanines such as dipotassium phthalocyanine dissolve in oxygen-donor solvents such as diethylene glycol dimethyl ether and dimethylformamide or in solvents containing oxygen-donor ligands to give solutions which may be used in a manner analogous to the abovementioned method of using dilithium phthalocyanine solutions. The solutions in oxygen-donor solvents contain oxygen-donor metal phthalocyanine complexes, for example K$_2$Pc (diglyme)$_2$ and K$_2$Pc(DMF)$_4$, which may be isolated and used as solutions in other solvents if desired. Complexes of dipotassium phthalocyanine with crown ethers such as 18-crown-6 may be used as solutions in aromatic hydrocarbons such as toluene.

Some metal phthalocyanines, for example the Fe$^{II}$ derivative, form relatively stable adducts with Lewis bases such as pyridine. These adducts are soluble in solvents such as toluene and polar aprotic solvents, for example dimethyl sulphoxide. When such solutions are placed on an aqueous surface, conversion of the adduct to the insoluble metal phthalocyanine itself can take place under appropriate pH conditions.

Transfer of the phthalocyanine compound from the supporting liquid to the substrate, which can be of any appropriate material, is effected by dipping the substrate into the supporting liquid and withdrawing it again, so that the film of phthalocyanine compound adheres to the surface of the substrate. Provision of means for maintaining the integrity of the layer on the liquid is necessary and this can comprise a sweep or paddle, preferably responsive to a microbalance which constantly measures the surface pressure of the film. This feature of maintaining constant pressure upon the organic layer is important for the production of an aligned deposit upon the support.

If desired, the thin layer formed on the surface of the supporting liquid may include one or more other organic materials in addition to the phthalocyanine compound in which case a composite film is transferred to the solid substrate. Stearic acid is an example of a suitable organic material.

In order to facilitate transfer of the phthalocyanine compound from the supporting liquid to the solid substrate, it is sometimes advantageous to include a less volatile organic liquid with the volatile solvent. This higher boiling liquid should be miscible with the solvent and, like the solvent, should be inert with respect to the other ingredients and be less dense than and immiscible with the supporting liquid. This less volatile liquid facilitates uniform transfer of the layer of phthalocyanine compound. Suitable compounds for this purpose include mesitylene, 2-methylnaphthalene, chlorinated hydrocarbons such as trichlorobenzenes and 1-chloronaphthalene and other liquids of similar boiling point. The use of such liquids permits the employment of higher surface pressures during transfer of the film to the substrate and so allows a higher rate of dipping.

The deposited film of the phthalocyanine compound may be employed as such, but it will sometimes be found desirable to increase its thickness by repeated applications of layers of the same material or by, say, interlaying with other materials to modify its properties. Thus, for some applications it may be appropriate to lay down a single layer of phthalocyanine compound forming a thin film, which in most cases will be of monomolecular dimensions, on the substrate. While the Applicants do not wish to be bound by any particular theory, it is believed that in most cases in the films produced by the method of the invention, the phthalocyanine molecules are arranged in monolayers in which the edges or the major faces of the molecules are adjacent to the substrate surface depending upon the nature of the substrate. Depending, therefore, upon the molecular size of the particular phthalocyanine compound employed, which itself is dependent upon the nature and number of any substituents and the nature of the substrate used, it is possible to produce monomolecular films, free from imperfections, having thicknesses typically in the range 5 to 20Å.

Accordingly, no difficulty is experienced in producing phthalocyanine films thinner than the thinnest films (40Å) mentioned in the prior art. Such very thin films, in addition to being valuable in many electronic devices, are useful in gas detection devices because of their enhanced response times and reduced recovery times. If desired, the sensitivity may be further enhanced by incorporating the film within an electric field effect device.

For other applications, thicker films may be required in which case the substrate is repeatedly dipped so as to form a film comprising a plurality of monomolecular layers. In this way, films having a thickness of 100Å or more can be produced depending upon the number of layers deposited. Whilst thick films of phthalocyanine compounds have been reported previously, those produced by the method of the invention are much superior on account of their completely uniform thickness. The variations in film thickness which inevitably result from prior art methods of deposition are substantially eliminated and accordingly the manufacture of improved electronic and other devices is made possible.

Substrates to which the phthalocyanine films may be applied include electrical conductors, insulators and semiconductors. As examples of inorganic materials, there may be mentioned metals, metal oxides, glass and especially those used in electronic devices, particularly silicon, cadmium telluride and associated insulators. As examples of organic materials there may be mentioned plastics materials including metallised plastics materials, for example aluminised polyethylene terephthalate.

The invention is useful for applying thin films of phthalocyanine compounds to substrates for a variety of purposes. In some cases, the phthalocyanine film may be a passive component of a composite article having a decorative or protective function or acting as an insulating material in an electrical device. In other cases, the film will be an active component of a composite article, for example in an electronic, electrical, electrochemical or photochemical device. The films are especially useful for the spectral sensitisation of photoreceptors such as solar cells and photoconductors and also in devices for the detection of gases such as ammonia, sulphur dioxide, nitrogen oxides, halogens and hydrogen halides.

Specific devices in which phthalocyanine films prepared as described herein may advantageously be used include devices incorporating protective and dye-sensitising coatings, optical filters, photoconductors including radiation detectors, photovoltaic cells (MIS and p-n junction types), xerographic photoreceptors and other imaging systems, semiconductor devices including Schottky barriers, varactors, gate-controlled diodes, charge-coupled devices and field effect transistors, electron-tunnelling devices, MIM capacitors including superconducting junctions, chemically sensitive semiconductor devices, gas detectors, valve grinding structures, information storage devices and catalytic surfaces.

In devices such as those mentioned above, the phthalocyanine films are notable for their excellent stability, especially thermal stability, compared with other compounds having similar properties, and excellent adhesion to a variety of substrates.

The invention is illustrated but not limited by the following Examples.

EXAMPLE 1

Dilithium phthalocyanine (prepared by the method of Barrett, Frye and Linstead—J. Chem. Soc.; 1937, 1157–1163 but using n-hexanol in place of amyl alcohol) was dissolved in acetone to give a 0.27 g/l solution which was then diluted with an equal volume of pure dry chloroform. (All organic solvents were thoroughly dried over molecular sieves before use). The resulting deep blue solution was passed through a fine filter to remove any particulate material and moisture was carefully excluded to prevent premature hydrolysis of the lithium compound.

A small volume (0.6 ml) of the solution was carefully added dropwise over a period of about 5 minutes to the surface of water (pH 5.0) contained in a Langmuir trough. The area of the aqueous surface was 286 $cm^2$ and the movable barrier (formed by a constant perimeter continuous band as described by Roberts, Vincett and Barlow in Phys. Technol. Vol 12, 1981, 69–75) had a maximum compression ratio of 5:1. After the solution had spread on the surface of the water, the organic solvents were allowed to evaporate over a period of 5–10 minutes.

The area enclosed by the barrier was then reduced and the surface pressure was recorded as a function of the enclosed surface area. The resulting isotherm, obtained at 25° C., is shown in FIG. 1. The absence of an intermediate region between the horizontal and steeply rising portions of the isotherm indicates that there is no tendency for the molecules in the film to slide over each other suggesting that the major faces of the molecule are not in the same plane as the surface of the water. The area occupied by the molecule ($>14Å^2$) in the film (obtained by extrapolating the steeply rising part of the curve to zero pressure) is less than the surface area of the edge or face of the phthalocyanine molecule which could indicate that the molecules in the film are stacked. Using this solution, similar values for the area occupied per molecule are obtained under a wide range of film preparation conditions. However, the concentration of the phthalocyanine solution is not known with sufficient accuracy to permit a conclusive statement on the question of stacking.

A glass microscope slide that had been thoroughly cleaned with isopropanol was coated with a phthalocyanine film by immersing it in the water contained in the Langmuir trough and then slowly withdrawing it (1 mm per minute) after the barriers had been adjusted to give a surface pressure of 20 dynes/cm. The coated slide was then allowed to dry in air. Further coatings were applied by first opening the barriers, immersing the slide, adjusting the barriers to 20 dynes/cm and slowly withdrawing the slide.

Figure 2:
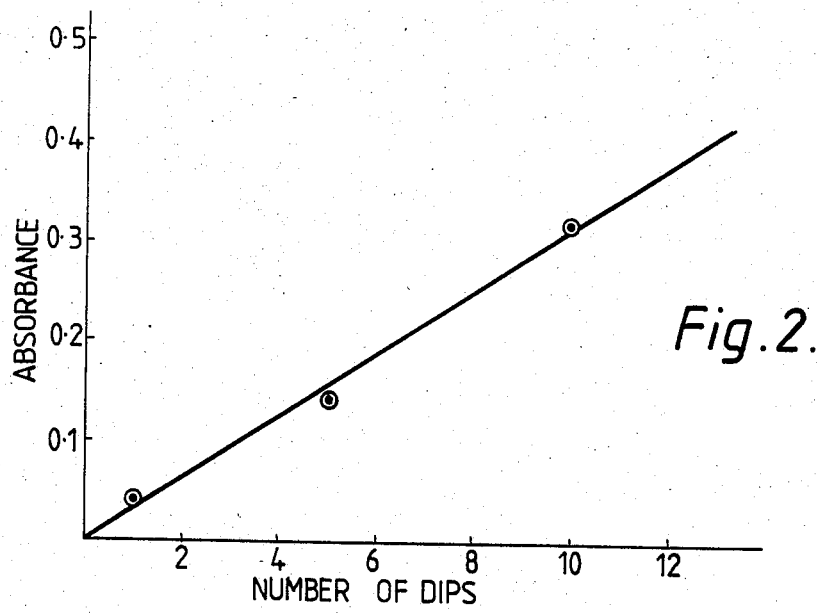

The coated slide displayed a slight green/blue hue which, in marked contrast to conventional Langmuir films, was particularly difficult to remove by physical rubbing or chemical attack. Electron microscopy showed that the phthalocyanine film was uniformly deposited on the glass and it displayed an ultra violet/visible spectrum similar to that of an evaporated film of phthalocyanine (broad λ max 325, 650 nm). Moreover, as shown in FIG. 2, the absorbance at 650 nm of a coated slide increased uniformly with the number of dips applied to it, demonstrating that films of phthalocyanine can be deposited one on top of another and also that the thickness per dip is constant.

On increasing the rate of withdrawal of the slide, higher pressures are required, sometimes leading to fragmentation of the rigid films. This can be overcome by addition of a slowly-evaporating liquid such as mesitylene, transfer rates of up to 5 mm per minute then being possible without fragmentation of the film.

EXAMPLE 2

Figure 3:
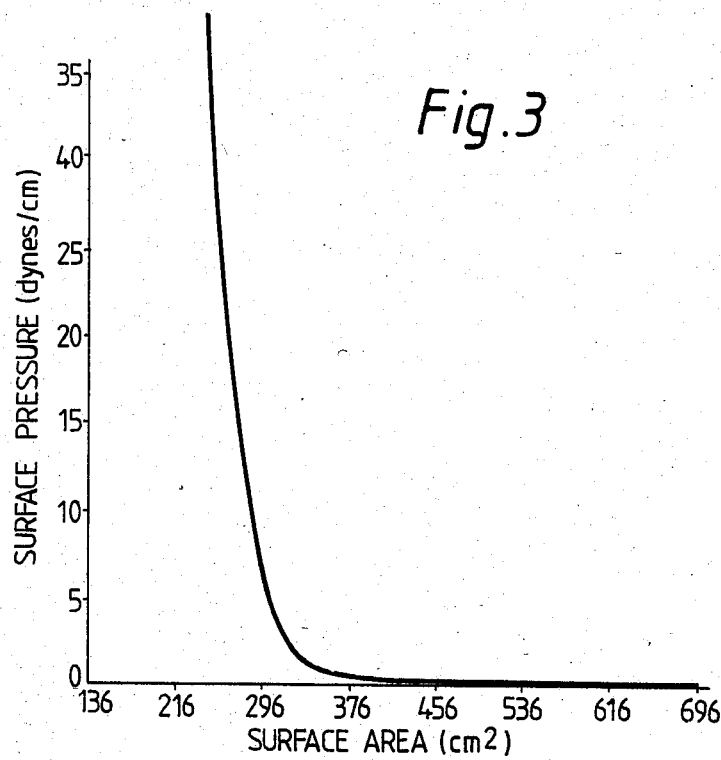

A tertiary butyl substituted metal-free phthalocyanine (4 t-butyl groups per molecule) was dissolved in toluene and the solution then diluted with an equal volume of chloroform. The concentration of the resulting blue solution was $8.1 \times 10^{-4}$ mol $1^{-1}$ and it displayed a typical phthalocyanine visible spectrum, $\lambda$ max 698,661 (shoulder), 641,598 and 338 nm. A portion of the solution (176 µl) was carefully added to the surface of water (pH 5.58) in the Langmiur trough at 18.5° C. After about 2 minutes the film was compressed by reducing the surface area containing the film as described in Example 1 and from the resulting isotherm, shown in FIG. 3, the area occupied by a single molecule of the phthalocyanine compound is calculated to be 38Å$^2$. The area estimated from molecular models is about 100Å$^2$ for a single isolated molecule of H$_2$PcBu$^t_4$ with its edge to the aqueous surface. With this compound there is evidence of molecular stacking as the pressure in the film is increased. This stacking is reversible as the pressure is decreased.

A glass microscope slide carefully cleaned with isopropanol was coated with the phthalocyanine film by immersing it in the Langmuir trough and withdrawing at about 3 mm per minute while maintaining a surface pressure of about 20 dynes/cm. After allowing the coated slide to dry in air, further coatings were applied by repeating the process.

Figure 5:
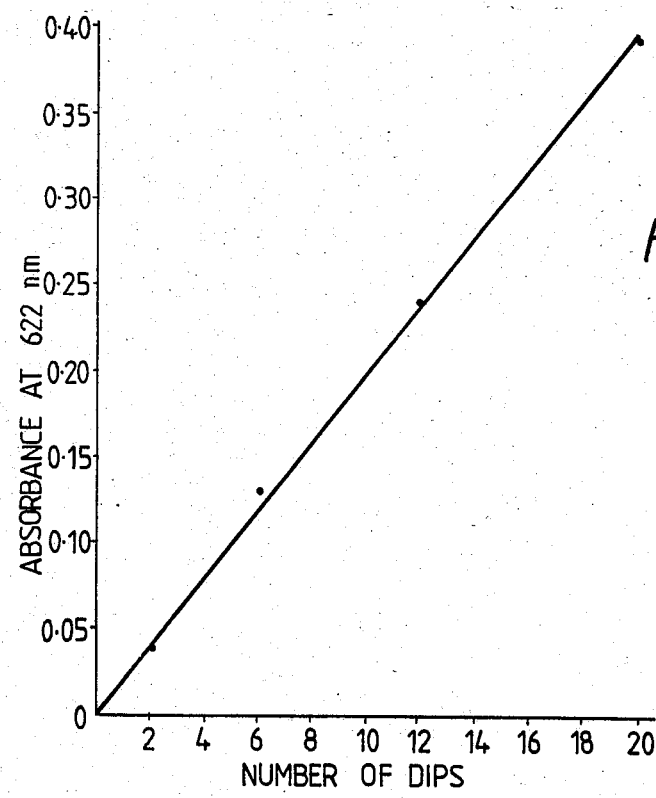
Figure 4:
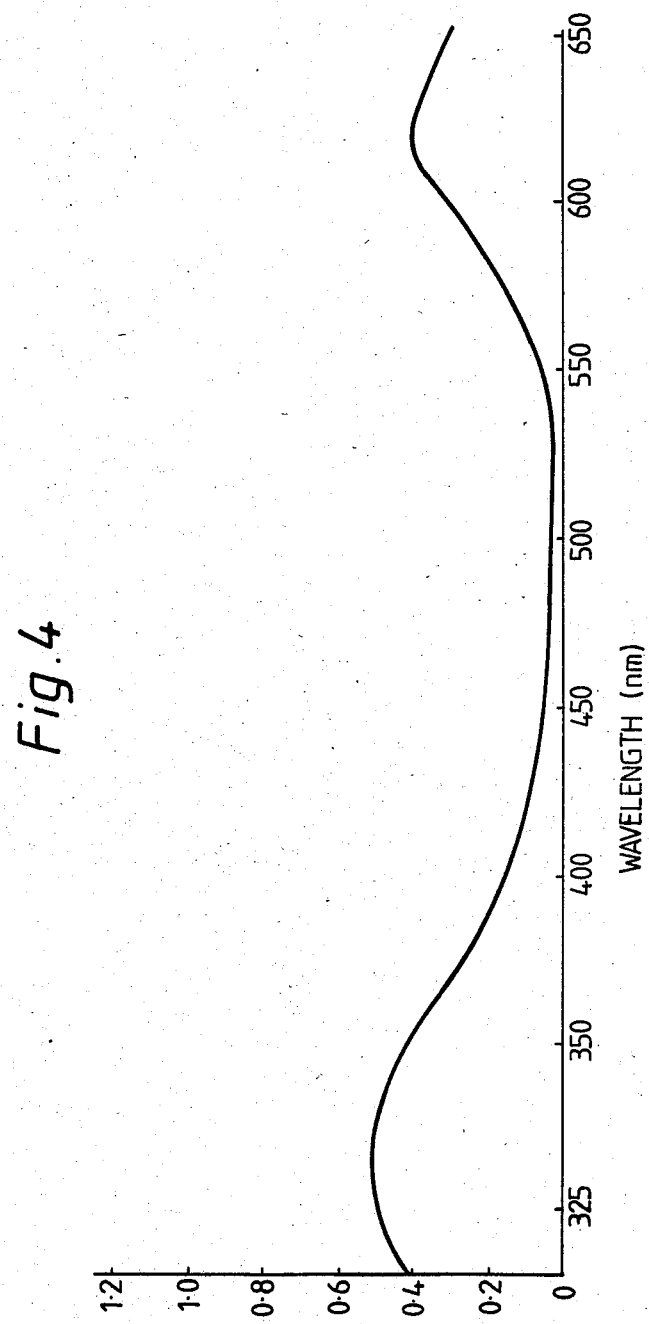

The visible spectrum of films so produced displayed broad maxima at 332 nm and 622 nm (FIG. 4) and the absorbance at any particular wavelength increased uniformly with the number of layers applied (FIG. 5 for $\lambda$ max = 622 nm) showing that when required many layers may be deposited on to a substrate and that each layer has the same thickness.

Films may be similarly applied to a range of materials including semi-conductors such as indium phosphide.

The electrical properties of phthalocyanines are known to be markedly dependent on the presence of trace impurities, their history and immediate environment. The electrical resistivities of films of H$_2$PcBu$^t_4$ prepared in the way described above compare favourably with values obtained for extremely carefully prepared conventional phthalocyanine samples.

EXAMPLE 3

Figure 6:
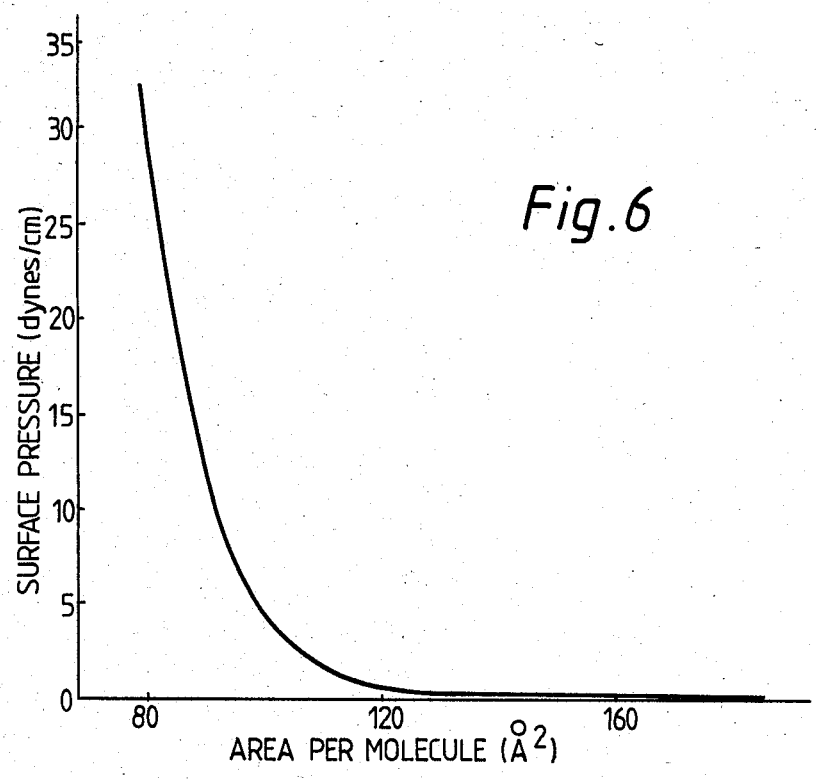

The tetra-tert-butyl derivative of zinc phthalocyanine (ZnPcBu$^t_4$) was dissolved in pure chloroform (5.27 mg in 5 ml) to form a bright blue solution displaying a typical metal phthalocyanine visible spectrum ($\lambda$ max 675 nm, 610 nm and 344 nm with a pronounced shoulder at 646 nm). A small amount of this solution (70.5 µl) was carefully added to the surface of water (pH 5.6) at 19.5° C. in Langmuir trough, the surface area being 1058 cm$^2$. After allowing the chloroform to evaporate from the surface (5 min), the film so formed was compressed in the usual way and from the isotherm obtained (FIG. 6), the area occupied by a molecule in the film was calculated to be 97.2Å$^2$. Repeated experiments using solution containing 9.88 mg/10 ml of the phthalocyanine yielded values of 92.0Å$^2$ and 94.4Å$^2$ indicating that the phthalocyanine molecules were present as a monolayer with their edges on the aqueous surface (the calculated value from molecular models is about 100Å) and almost certainly inclined as in the known solid state structures of unsubstituted phthalocyanines there being no evidence of molecular stacking in the film. These films were readily transferred to glass or metal substrates and multiple layers could easily be built up by sequential dips. The coated substrates had a visible blue coloration.

EXAMPLE 4

An aluminium coating was applied by vacuum sublimation to a glass microscope slide (76 mm in length, the coating having a thickness of 300Å and a natural oxide surface. A layer of ZnPcBu$^t_4$ was then applied over a length of 39 mm of the slide (measured from one end) by transfer from the aqueous surface of a Langmuir trough as already described. Two further layers of the phthalocyanine were applied over a length of 26 mm of the slide followed by two more layers over a length of 13 mm (both measurements being from the same end as previously). In this way, regions of 1, 3 and 5 layers, each region being 13 mm in length, were produced on the slide. During the transfer of the phthalocyanine film from the aqueous surface to the aluminium/aluminium oxide surface, the area occupied per phthalocyanine molecule increased, typically by a factor of about 1.86. This was taken to indicate that the orientation of the molecules in the monolayer on the hydrophobic oxide surface was tending towards facial rather than edgewise.

Several circular gold electrodes (2 mm diameter, 150Å thickness) were deposited by vacuum sublimation on to each of the areas coated with the phthalocyanine and the electrical capacitance between the gold electrodes and the aluminium was measured using a Wayne Kerr bridge (model B900). The results (as averages of several measurements) were as follows:

| No of layers | Capacitance |
| --- | --- |
| 1 | 24.35 nF |
| 3 | 17.28 nF |
| 5 | 12.78 nF |

Figure 7:
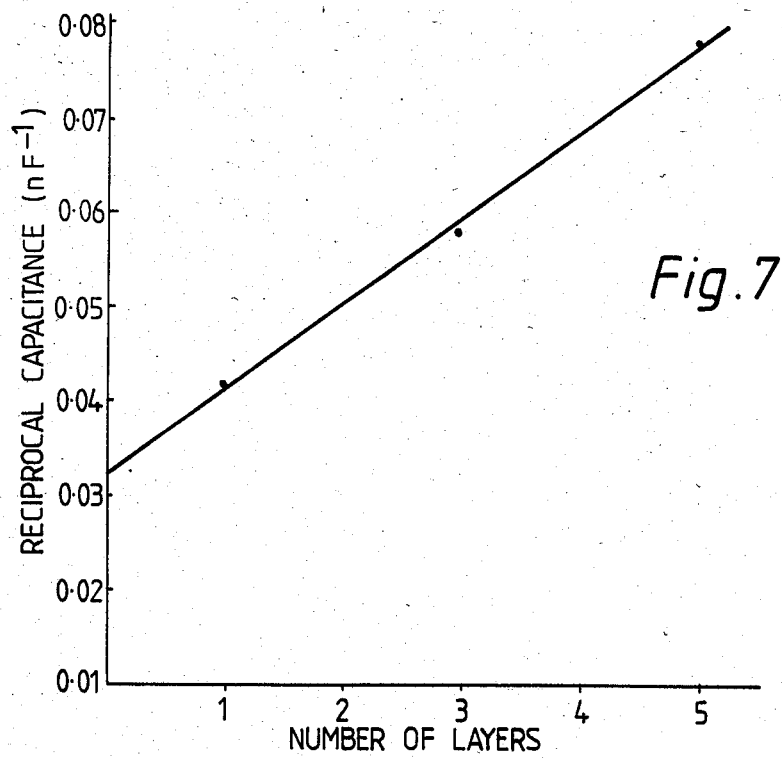

FIG. 7 is a graph of reciprocal capacitance against number of layers. The linearity of the relationship (gradient $0.92 \times 10^{-2}$ nF$^{-1}$) demonstrates the reproducibility of monolayer capacitance and hence monolayer thickness. Assuming the dielectric constant of ZnPcBu$^t_4$ in these layers is the same as for $\beta$-copper phthalocyanine (cf. J. Chem. Phys., 57, 5033, (1972)), a value of 11.5Å is calculated from these data for the thickness of a single ZuPcBu$^t_4$ layer on the aluminium/aluminium oxide surface indicating again that the molecular orientation is tending to be facial to the surface.

EXAMPLE 5

Nine layers of ZnPcBu$^t_4$ were applied to a carefully degreased and washed glass slide by transfer from the aqueous surface of a Langmuir trough as already described. Two gold electrodes, 10 mm $\times$ 5 mm and having a thickness of 150Å were deposited on the phthalocyanine surface so that there was a 0.25 mm gap between the 10 mm slides of the electrodes. The resulting structure is illustrated in FIGS. 8a and 8b of the accompanying drawings.

Figure 8A:
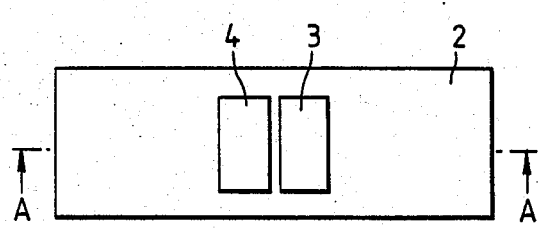
Figure 8B:
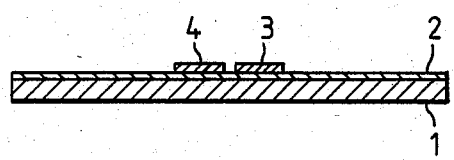

FIG. 8a shows a plan view of the structure and FIG. 8b shows a cross-sectional view along the line AA.

The structure comprises a glass substrate 1 (not shown in FIG. 8a) bearing a phthalocyanine film 2 which in turn carries two gold electrodes 3 and 4.

The electrical resistance (19.5° C., 10 volts) between the gold electrodes in air was $2.0 \times 10^{11}$ ohms. Exposure to air containing 100 ppm of ammonia produced an immediate decrease in the resistance to one-sixth of the original value (to $3.3 \times 10^{10}$ ohms). When the ammonia-containing air was replaced by ammonia-free air, the resistance rose to $1.5 \times 10^{11}$ ohms within about 15 seconds and had regained its original value after about 30 seconds.

EXAMPLE 6

Figure 9:
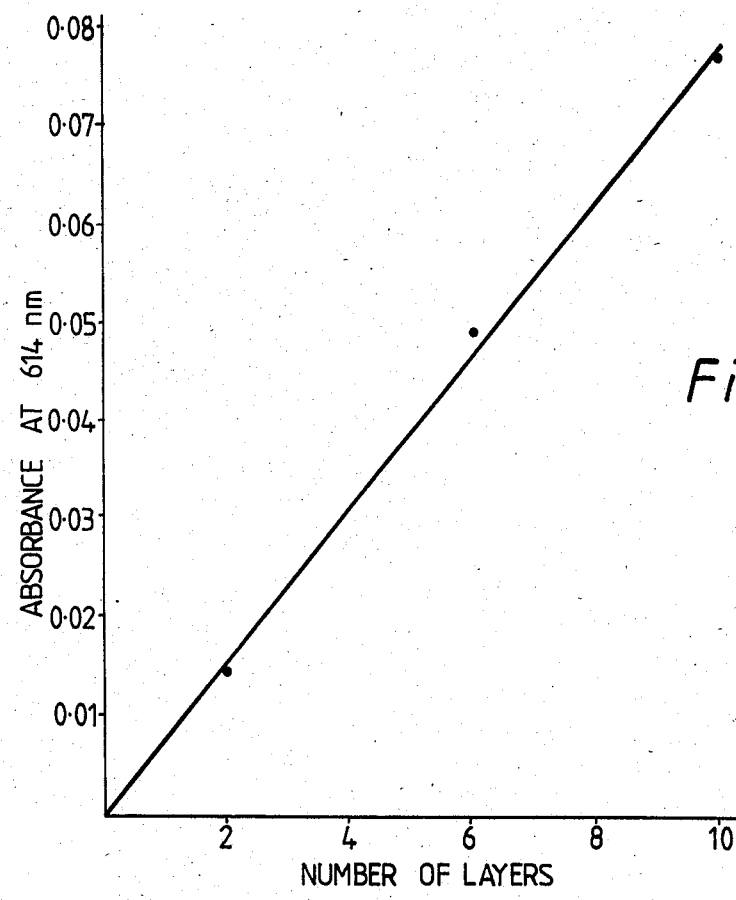

The tetra-tert-butyl derivative of copper phthalocyanine was dissolved in pure chloroform (2.5 mg/5 ml) to form a bright blue solution displaying a typical metal phthalocyanine visible spectrum ($\lambda$ max 676, 610, 336 nm with a prounounced shoulder at 646 nm). Small amounts of this solution were carefully added to the surface of water contained in the Langmuir trough to form monolayer films as previously described for $ZnPcBu^t_4$. These layers were readily transferable to solid substrates, a glass microscope slide coated with 10 layers showing an absorbance maximum at 614 nm in the visible spectrum. The linear relationship between the absorbance at 614 nm and the number of layers applied to the slide is shown in FIG. 9.

When films of $CuPcBu^t_4$ were transferred from the water surface in the Langmuir trough to a clean glass substrate, the area occupied per molecule remained approximately the same. However, on transfer to an aluminium/aluminium oxide surface, the area occupied per molecule more than doubled. Typically the ratio of the molecular area on water to the area on the substrate was 1:0.95 for glass and 1:2.27 for aluminium demonstrating the substrate dependent orientation of the film.

Electrical capacitance measurements on a $CuPcBu^t_4$ film on aluminium/aluminium oxide were carried out as described for $ZnPcBu^t_4$ in Example 4 and provided an estimated monolayer thickness of 7Å for $CuPcBu^t_4$ on this substrate.

EXAMPLE 7

A device of the type described in Example 5 and illustrated in FIGS. 8a and 8b was prepared by applying 3 layers of $CuPcBu^t_4$ to a glass slide and depositing two gold electrodes. The D.C. resistance (10 volts) between the gold electrodes in air was $3 \times 10^{11}$ ohms. On exposure to air containing 100 ppm of ammonia, the resistance immediately fell to $6.7 \times 10^{10}$ ohms. Displacement of the ammonia-containing air with pure air produced a rapid recovery in the observed resistance as shown below:

| Time (s) | NH$_3$ (ppm) | Resistance (ohms) |
|---|---|---|
| 0 | 100 | $6.7 \times 10^{10}$ |
| 8 | 0 | $1.6 \times 10^{11}$ |
| 13 | 0 | $2.5 \times 10^{11}$ |
| 30 | 0 | $3 \times 10^{11}$ |

A similar device using only one layer of the phthalocyanine compound displayed a more than tenfold change in resistance on exposure to air containing 3000 ppm of ammonia together with a very rapid recovery when the ammonia-containing air was replaced by ammonia-free air. By contrast, devices containing the thicker films described in the prior art display much longer recovery times because of absorption of the gas being measured.

Similar rapid changes in resistance were obtained when a device of the type described was exposed to halogens and hydrogen halide vapours. The recovery time was again very short.

We claim:

1. A method of preparing a thin film of a phthalocyanine compound on a substrate which comprises forming a thin layer of the phthalocyanine compound on the surface of a suitable liquid by applying to said surface a solution of a soluble phthalocyanine compound in a volatile organic solvent or solvent mixture, the solvent or at least one component of the solvent mixture being immiscible with the liquid, and allowing the solvent or solvents to evaporate and subsequently passing the substrate through the layer of phthalocyanine compound.

2. A method according to claim 1 wherein the thin layer of phthalocyanine compound is formed on the surface of the liquid by applying to the surface of the liquid a solution of phthalocyanine compound in a volatile organic solvent which is less dense than, and immiscible with, the liquid and allowing the solvent to evaporate, the phthalocyanine compound having the formula:

$$Pc(Y)n$$

wherein Y is a solubilising group, n is an integer from 1 to 16 and Pc represents a phthalocyanine nucleus which may be metal-free or may contain a metal atom.

3. A method according to claim 2 wherein Y is a hydrocarbon group.

4. A method according to claim 3 wherein Y is a tertiary butyl group.

5. A method according to any one of claims 2 to 4 wherein the liquid is water.

6. A method according to claim 1 wherein the thin layer of phthalocyanine compound is formed on the surface of the liquid by applying to the surface of the liquid a solution of a first phthalocyanine compound which reacts with the liquid to form an insoluble second phthalocyanine compound.

7. A method according to claim 6 which comprises applying a solution of dilithium phthalocyanine in an organic solvent to an aqueous surface.

8. A composite article comprising a thin film of a phthalocyanine compound on a substrate, the film having been deposited on the surface of the substrate by a method according to claim 2, 3, 4, 6, 7 or 1.

9. An electronic, electrical, electrochemical or photochemical device comprising a thin film of a phthalocyanine compound on a substrate, the film having been deposited on the surface of the substrate by a method according to claim 2, 3, 4, 6, 7 or 1.

10. A device according to claim 9 having a gas detection capability.

11. A composite article comprising a thin film of a phthalocyanine compound on a substrate, the film having a thickness of less than 40Å.